United States Patent [19]
Konrad et al.

[11] Patent Number: 4,855,130
[45] Date of Patent: Aug. 8, 1989

[54] HAIR TREATING COMPOSITIONS AND PROCESSES FOR IMPROVING THE CONDITION OF HAIR

[75] Inventors: Eugen Konrad, Darmstadt; Herbert Mager, Fribourg; Dietrich Hoch, Pfungstadt, all of Fed. Rep. of Germany

[73] Assignee: Wella Aktiengesellschaft, Darmstadt, Fed. Rep. of Germany

[21] Appl. No.: 116,721

[22] PCT Filed: Jan. 20, 1987

[86] PCT No.: PCT/EP87/00026
§ 371 Date: Sep. 30, 1987
§ 102(e) Date: Sep. 30, 1987

[87] PCT Pub. No.: WO87/04616
PCT Pub. Date: Aug. 13, 1987

[30] Foreign Application Priority Data
Jan. 30, 1986 [DE] Fed. Rep. of Germany ....... 3602746

[51] Int. Cl.$^4$ ...................... A61K 7/06; A61K 7/075; A61K 7/08
[52] U.S. Cl. ............................. 424/70; 252/DIG. 13; 424/71
[58] Field of Search .................................. 424/71, 70; 252/DIG. 13

[56] References Cited
FOREIGN PATENT DOCUMENTS

| 109711 | 7/1982 | Japan | ...................................... 424/70 |
| 8202337 | 7/1982 | PCT Int'l Appl. | . |
| 8704616 | 8/1987 | PCT Int'l Appl. | . |

*Primary Examiner*—Ellis P. Robinson
*Assistant Examiner*—Susan S. Rucker
*Attorney, Agent, or Firm*—Michael J. Striker

[57] ABSTRACT

The subject matter of the invention is a composition and a process for improving the condition of hair are improved based on a synergistic combination of glycine with a physiologically compatible aliphatic organic acid which is free of amino groups, particularly citric acid, and a wax and/or oil component, particularly a mixture of petrolatum and fatty alcohols.

The combination of glycine, physiologically compatible aliphatic organic acid which is free of amino groups, and wax and/or oil components, which combination has a hair conditioning action, is completely harmless physiologically and can also be used together with anionic surfactants. The compositions, according to the invention, act on the hair so as to disentangle it, smooth the hair surface and improve the feel as well as the ability of the hair to be combed.

7 Claims, No Drawings

HAIR TREATING COMPOSITIONS AND PROCESSES FOR IMPROVING THE CONDITION OF HAIR

DESCRIPTION

The invention is directed to hair treating compositions based on a synergistic combination of glycine, an aliphatic organic acid which is free of amino groups, and a wax and/or oil component. The subject matter of the patent application is also a process for improving the condition of the hair.

The structure of the hair is damaged by means of frequent bleaching, permanent waving and dyeing and frequent washing of the hair with degreasing surfactants. The hair becomes brittle and it loses its luster. Moreover, the hair is charged with static electricity during combing and the roughened hair surface causes matting and knotting of the hair. This makes combing much more difficult.

Hair treating compositions which act so as to improve combing ability and care for the hair have therefore achieved considerable importance. For example, such compositions are frequently distributed in the hair after washing while it is still wet in the form of a clear hair care rinse or in the form of an emulsion, as so-called cream rinse, allowed to act for a period of several minutes to an hour, and then rinsed out with water.

Cationic surfactants, particularly quaternary ammonium compounds such as cetyltrimethylammonium chloride are primarily used in combination with various wax-like additions, for example, petrolatum, fatty alcohols, and fatty acid esters, as active ingredients for improving the structure of the hair.

However, hair treating compositions based on the aforementioned conditioning active ingredients have satisfactory results only in the treatment of dry and porous hair. They are less well-suited for the treatment of hair which rapidly becomes greasy again, since the natural regreasing of the hair is reinforced through their application, so that the holding ability of the hair styling is worsened in turn.

The reasons for the heavy regreasing of the hair are, on the one hand, the residue of the hair treating composition remaining in the hair after rinsing, and, on the other hand, the cationic emulsifiers contained in these compositions. The cationic emulsifiers absorbed by the hair cause a waterproofing of the hair surface so that the secretions of the sebaceous glands can be distributed in the hair more rapidly. Moreover, because of their incompatibility with anionic surfactants, cationic emulsifiers cannot be worked into hair treating compositions with a content of these surfactants, as in many shampoos or hair dyeing compositions, for example.

It is to be noted, in addition, that cationic surfactants, as a rule, have a poor compatibility with skin and mucous membranes. For this reason, the effectiveness of the conventional cream rinse on the hair can be increased only to a limited extent by means of increasing the concentration of surfactants.

It has already been tried repeatedly to avoid the aforementioned disadvantages by means of applying amino acids, such as a slightly acidic mixture of various amino acids and vitamins (see U.S. Pat. No. 4,201,235), as a hair conditioning component in hair treating compositions. However, it is very costly and expensive to produce these mixtures consisting of a plurality of various vitamins and amino acids.

Moreover, the use of keratin hydrolyzates and citric acids in a "neutralizing shampoo" is known from the text "Cosmetics & Toiletries", vol. 98 (1983), pages 59 to 68. However, this shampoo has only a slight hair caring action and leads to a considerable drying out of the hair. For this reason, a subsequent, possibly even repeated treatment with a hair conditioning composition is required after washing the hair.

It is also known from the text W. Fassbender, Parfumerie und Kosmetik [manufacture of perfumes and cosmetics] 39 (1), pages 11 to 16 (1958) that amino acid sols containing 18 to 22 different amino acids can be used in pharmaceutics and cosmetics, for example, in skin treating and hair care compositions which are adjusted so as to be slightly acidic. The production of these amino acid sols is effected by means of fractionated hydrolysis of natural proteins and subsequent purification of the contained hydrolyzates. It is therefore difficult to ensure the uniform composition of the amino acid sols, which is important for the quality of cosmetic compositions.

SUMMARY OF THE INVENTION

It is the object of the present invention to provide a hair treating composition and a hair treating process based on more suitable active ingredients which condition the hair and accordingly to eliminate the disadvantages described above.

In keeping with these objects and with others which will become apparent hereinafter, one feature of the present invention resides in a hair treating composition, characterized in that it contains a combination of
 (a) 0.5 to 25 percent by weight, preferably 3.0 to 15 percent by weight, glycine,
 (b) 1.0 to 10 percent by weight, preferably 0.5 to 5.0 percent by weight of physiologically compatible aliphatic organic acid which is free of amino groups and
 (c) 0.5 to 10 percent by weight, preferably 1.0 to 5.0 percent by weight, wax and/or oil components.

In accordance with another feature of the present invention a process is proposed for improving the composition of the hair, characterized in that the hair is treated with the above described treating composition at a temperature of 15 to 60 degrees Celsius.

The novel features which are considered as characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

It has now been found in a completely surprising manner that the proposed object has been met in an outstanding manner by hair treating compositions which are characterized in that they contain a combination of
 (a) 0.5 to 25 percent by weight, preferably 3.0 to 15 percent by weight, glycine,
 (b) 1.0 to 10 percent by weight, preferably 0.5 to 5.0 percent by weight, physiologically compatible aliphatic organic acid which is free of amino groups and (c) 0.5 to 10 percent by weight, preferably 1.0 to 5.0 percent by weight, wax and/or oil components.

A particularly preferred embodiment form of the invention is a hair care emulsion which contains a combination of (a) 3.0 to 15 percent by weight glycine,
(b) 0.5 to 5.0 percent by weight citric acid and
(c) 1.0 to 5.0 percent by weight of a 1:1 mixture of petrolatum and fatty alcohols.

No satisfactory hair conditioning characteristics can be established in hair treating compositions based only on glycine, or only on a physiologically compatible aliphatic organic acid which is free of amino groups, or only on a wax and/or oil component, or only on a combination of two of these three components contained in the composition according to the invention. On the other hand, the hair treating compositions, according to the invention, which are based on a synergistic combination of glycine with a physiologically compatible aliphatic organic acid which is free of amino groups and a wax and/or oil component, have an outstanding action which improves combing ability without loading the hair. In particular, the ability to comb the hair when wet is substantially improved by means of these compositions. Moreover, they act on the hair in an astringent manner and with a disentangling effect, smooth the hair surface and improve the feel of the hair.

The favorable hair conditioning characteristics of the compositions according to the invention are particularly surprising because they contradict the opinion expressed in W. Fassbender, Kosmetik und Parfumerie 39 (1), pages 11 to 16 (1958), according to which the use of individual isolated amino acids in cosmetic preparations are completely pointless, if not actually harmful.

The compositions, according to the invention, are free of cationic surfactants which irritate skin. Glycine, an amino acid which is compatible with the skin and promotes cell growth, is used instead.

Examples for suitable physiologically compatible aliphatic organic acids contained in the compositions described here, which aliphatic organic acids are free of amino groups, are particularly aliphatic organic acids which are soluble in water or water and alcohol, such as lactic acid, tartaric acid, pimelic acid, adipic acid, malonic acid, succinic acid, glutaric acid, glyoxylic acid and citric acid, of which the latter is particularly preferred.

Wax components which are suitable for use in the hair treating compositions according to the invention are, for example, wool wax (adeps lanae), beeswax, higher fatty alcohols, such as cetyl and stearyl alcohols, and petrolatum (a mixture of paraffins and hydrocarbon oils which melts at 35 to 45 degrees Celsius), whereas paraffin oil and fatty acid esters, such as glycerine esters of palmitic, stearic and oleic acid, can be used as oil components.

The wax and oil components can be used alone or in combination with one another in the hair treating compositions according to the invention. The use of a 1:1 mixture of petrolatum and fatty alcohols is particularly advantageous.

The hair treating compositions described in the application can be present in any desired preparation form which is suitable for hair treatment, for example, in the form of a lotion, emulsion or a gel. Preferred preparations are hair rinses, hair care emulsions, hair tonic packs, hair strengtheners or shampoos. But the hair treating compositions according to the invention can also be in the form of hair dyestuffs, hair tinting compositions or fixing agents for the shaping of hair.

This involves preparations which remain in the hair for shorter or longer periods of time depending on their purpose.

Because of their content of the above-described active ingredient combination of glycine, a physiologically compatible aliphatic organic acid, which is free of amino groups, and wax and/or oil components, the treated hair is conditioned at the same time. However, preparations which are used chiefly or exclusively for the purpose of improving the composition of the hair structure are particularly preferred.

The composition of these cosmetic preparations constitutes a mixture of the conditioning combination of glycine, a physiologically compatible aliphatic organic acid which is free of amino groups, and a wax and/or oil component with additional components conventionally used for hair treating compositions.

The following are particularly taken into consideration as conventional components of hair treating compositions: water, lower aliphatic alcohols, such as ethanol, propanol and isopropanol, polyhydric alcohols, such as glycerine and propylene glycol, anionic, amphoteric or nonionogenic surfactants, such as fatty alcohol sulfates, fatty alcohol ether sulfates, alkylsulfonates, alkylbenzenesulfonates, fatty acid taurides, oxyethylated fatty alcohols, oxyethylated alkylphenols, fatty acid alkanol amides, in addition to natural, modified natural or synthetic polymers, such as shellac, alginates, gelatins, pectins, cellulose derivatives, chitosan, polyvinylpyrrolidone, polyvinylacetate, acrylic acid or methacrylic acid polymerizates, basic polymerizates of esters from acrylic acid or methacrylic acid with amino alcohols, or the salts or quaternization products of these basic polymerizates, polyacrylonitrile and copolymerizates from such compounds, such as polyvinylpyrrolidonevinylacetate, in addition to thickeners, such as starches and cellulose derivates, as well as hair care materials such as lanolin derivates, cholesterin and pantothenic acid, in addition to dyestuffs, pigments, perfume oils, antioxidizing agents and preservatives.

The glycine salts contained in the hair treating compositions according to the invention do not act in a manner which is resistant to emulsions, even in the relatively high concentrations indicated here. Rather, it has been established in a surprising manner that the addition of glycine and a physiologically compatible aliphatic organic acid which is free of amino groups, particularly citric acid, acts in a manner which increases the viscosity and promotes the stability of the emulsions.

Another advantage of these hair treating compositions is their considerably improved compatibility with the eyes and skin compared with compositions based on the conventional cationic hair conditioning active ingredients, such as fatty acid alkyltrimethylammonium salts.

The present invention is directed, moreover, to a process for improving the condition of the hair which is characterized in that the hair is treated with a sufficient quantity of a hair treating composition, according to the invention, described above, generally approximately 25 to 50 grams, at a temperature of approximately 15 to 60 degrees Celsius. If this is not a hair treating composition which is intended to remain in the hair permanently, the hair is subsequently rinsed with warm water and treated further in a conventional manner.

The following examples explain the subject matter of the present invention in more detail:

EXAMPLES

| Example 1 | Hair Rinse |
|---|---|
| 10.00 g | glycine |
| 5.00 g | citric acid, anhydrous |
| 1.20 g | cetylstearyl alcohol |
| 1.20 g | petrolatum |
| 0.60 g | lauryl alcohol, oxyethylated twice |
| 0.20 g | salicylic acid |
| 0.15 g | sodium cetylsulfate |
| 0.15 g | sodium stearylsulfate |
| 0.50 g | perfume oil |
| 81.00 g | water |
| 100.00 g | |

35 g of the aforementioned hair rinse is distributed on very matted, very porous hair which has been dried with a towel after washing. A clear disentangling of the hair is observed already during the application of the hair rinse. After allowing it to act for a short period of time, the hair is thoroughly rinsed with warm water. A very smooth, cosmetically pleasant feel of the hair and a very good combing ability when wet is achieved by means of this treatment.

| Example 2 | Hair Care Emulsion |
|---|---|
| 5.00 g | glycine |
| 2.50 g | citric acid, anhydrous |
| 1.20 g | cetylstearyl alcohol |
| 1.20 g | petrolatum |
| 0.60 g | lauryl alcohol, oxyethylated twice |
| 0.50 g | perfume oil |
| 0.20 g | salicylic acid |
| 0.15 g | sodium cetylsulfate |
| 0.15 g | sodium stearylsulfate |
| 88.50 g | water |
| 100.00 g | |

The application of this hair care emulsion is effected in the same manner as in example 1.

The hair is clearly less matted and can be combed more easily. The effectiveness of this hair care emulsion is somewhat lower than that of the hair rinse according to example 1 because of the reduced content of glycine and citric acid, but it is completely satisfactory.

It will be understood that each of the elements described above, or two or more together, may also find a useful application in other types of compositions differing from the types described above.

While the invention has been illustrated and described as embodied in hair treating compositions and processes for improving the condition of hair, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A hair treating composition which is free of cationic surfactants comprising
   (a) 0.5 to 25 percent by weight glycine,
   (b) 1.0 to 10 percent by weight of a physiologically compatible aliphatic organic acid which is free of amino groups,
   (c) 0.5 to 10 percent by weight of a substance selected from the group consisting of wax, an oil component or both; and
   (d) balance additional components conventionally used for hair treating compositions selected from the group consisting of water, lower aliphatic alcohols, polyhydric alcohols, anionic, amphoteric, or nonionogenic surfactants, natural, modified natural or synthetic polymers, thickeners, hair care materials, dyestuffs, pigments, perfume oils, antioxidizing agents, and preservatives.

2. Hair treating composition according to claim 1, characterized in that the physiologically compatible aliphatic organic acid which is free of amino groups is selected from the group consisting of lactic acid, tartaric acid, pimelic acid, adipic acid, malonic acid, succinic acid, glutaric acid and citric acid.

3. Hair treating composition according to claim 1, characterized in that it contains a 1:1 mixture of petrolatum and fatty alcohols as said substance.

4. Hair treating composition according to claim 1, characterized in that it contains 3.0 to 15 percent by weight glycine.

5. Hair treating composition according to claim 1, characterized in that it contains 0.5 to 5.0 percent by weight physiologically compatible aliphatic organic acid which is free of amino groups.

6. Hair treating composition according to claim 1, characterized in that it contains 1.0 to 5.0 percent by weight of the substance selected from the group consisting of wax, an oil component and both.

7. Hair care composition according to claim 1, comprising
   (a) 3.0 to 15 percent by weight glycine;
   (b) 0.5 to 5.0 percent by weight citric acid,
   (c) 1.0 to 5.0 percent by weight of a 1:1 mixture of petrolatum and fatty alcohols and
   (d) balance additional components conventionally used for hair treating compositions selected from the group consisting of water, lower aliphatic alcohols, polyhydric alcohols, anionic, amphoteric or nonionogenic surfactants, natural, modified natural or synthetic polymers, thickeners, hair care materials, dyestuffs, pigments, perfume oils, antioxidizing agents, and preservatives.

* * * * *